(12) United States Patent
Renier et al.

(10) Patent No.: US 9,283,284 B2
(45) Date of Patent: *Mar. 15, 2016

(54) USE OF CONJUGATES OF HYALURONIC ACID IN THE LOCAL TREATMENT OF HYPERPROLIFERATIVE SKIN DISEASES

(75) Inventors: Davide Renier, Abano Terme (IT); Susy Panfilo, Abano Terme (IT)

(73) Assignee: FIDIA FARMACEUTICI S.P.A., Abano Terme (IT)

( * ) Notice: Subject to any disclaimer, the term of this patent is extended or adjusted under 35 U.S.C. 154(b) by 267 days.

This patent is subject to a terminal disclaimer.

(21) Appl. No.: 12/666,286

(22) PCT Filed: Jun. 19, 2008

(86) PCT No.: PCT/IB2008/001706
§ 371 (c)(1),
(2), (4) Date: Mar. 9, 2010

(87) PCT Pub. No.: WO2009/001209
PCT Pub. Date: Dec. 31, 2008

(65) Prior Publication Data
US 2010/0204175 A1   Aug. 12, 2010

(30) Foreign Application Priority Data

Jun. 22, 2007 (IT) .............. MI2007A1267

(51) Int. Cl.
*A61K 31/728* (2006.01)
*A61P 17/00* (2006.01)
*A61K 47/48* (2006.01)

(52) U.S. Cl.
CPC ....... *A61K 47/4823* (2013.01); *A61K 47/48784* (2013.01); *A61K 47/48984* (2013.01)

(58) Field of Classification Search
None
See application file for complete search history.

(56) References Cited

U.S. PATENT DOCUMENTS

| | | | |
|---|---|---|---|
| 5,910,489 A * | 6/1999 | Falk et al. ........... | 514/54 |
| 6,103,704 A | 8/2000 | Falk et al. | |
| 6,515,016 B2 * | 2/2003 | Hunter ........... | 514/449 |
| 2004/0127470 A1 * | 7/2004 | Masferrer ........... | 514/165 |
| 2007/0149618 A1 * | 6/2007 | Cuevas Sanchez et al. .. | 514/553 |

FOREIGN PATENT DOCUMENTS

WO   WO-2004/035629 A2   4/2004
WO   WO-2007/014784 A2   2/2007

OTHER PUBLICATIONS

Kurwa, Habib A. et al., Journal of the American Academy of Dermatology, "A randomized paired comparison of photodynamic therapy and topical 5-fluorouracil in the treatment of actinic keratoses", 1999, vol. 41, pp. 414-418.*
MeSH Browser Record: National Library of Medicine—Medical Subject Headings, "Administration, Cutaneous", 2014 MeSH; also available at http://www.nlm.nih.gov/cgi/mesh/2014/MB_cgi?mode=&index=263&field=all&HM=&II=&PA=&form=&input=; website visited May 20, 2014.*
Leonelli, F. et al., Helvetica Chimica Acta, A New and Simply Available Class of Hydrosoluble Bioconjugates by Coupling Paclitaxel to Hyaluronic Acid through a 4-Hydroxybutanoic Acid Derived Linker, 2005, vol. 88, p. 154-159.*
Brown, M. at al., "Hyaluronic acid: A unique topical vehicle for the localized delivery of drugs to the skin", Journal of the European Academy of Dermatology and Venereology, May 2005, vol. 19, No. 3, pp. 308-318.

* cited by examiner

*Primary Examiner* — Fereydoun G Sajjadi
*Assistant Examiner* — Bahar Craigo
(74) *Attorney, Agent, or Firm* — Birch, Stewart, Kolasch & Birch, LLP

(57) ABSTRACT

The use is described of a conjugate between hyaluronic acid or a derivative thereof and antitumoral drugs for the preparation of pharmaceutical compositions for the topical treatment of hyperproliferative skin diseases.

4 Claims, 3 Drawing Sheets

USE OF CONJUGATES OF HYALURONIC ACID IN THE LOCAL TREATMENT OF HYPERPROLIFERATIVE SKIN DISEASES

The present invention relates to the use of conjugates of hyaluronic acid in the local treatment of hyperproliferative skin diseases.

In particular, the present invention relates to a new use of a conjugate between hyaluronic acid or derivatives thereof and antitumoral drugs, for the preparation of pharmaceutical compositions destined for the treatment of hyperproliferative dermatological pathologies, and more specifically for the treatment of actinic keratosis.

FIELD OF THE INVENTION

Actinic keratosis (AK), or solar keratosis, is a disease substantially caused by chronic exposure to sun radiation, particularly to ultraviolet radiation. Its symptoms are skin lesions mostly localized in areas mainly exposed to the sun; almost all the lesions consist of reasonably-sized plaques, with a dry and irregularly squamous surface. The base can be light or dark, brown-reddish, pink, red, but it may also be the same colour as the skin; in the latter case, the lesion is identified by touch as the squamous surface which is formed is dry and rough. The skin lesions are of the hyperkeratosic or parakeratosic type with the presence of a thick population of dysplasic keratinocytes.

Actinic keratosis is considered the prodromic phase of a much more serious and invasive and even metastasizing disease; there is in fact an epidemiological correlation between AK and squamous cell carcinoma, also known as spinocellular carcinoma. AK however is defined as a pre-cancerous situation, whose eradication must be carefully evaluated each time in relation to the risk of malignant degenerations.

The therapeutic approach to AK substantially consists in the removal of the hyperkeratosic areas and can be effected surgically/ablatively (cryotherapy, chemical peeling, curettage, dermoabrasion, laser) or pharmacologically. In the state of the art the most widely-used pharmacological solutions envisage the use of:
  retinoids, both topical and systemic, characterized however by relevant and serious side-effects and whose administration must therefore be carefully evaluated;
  local immunomodulators, such as imiquimod (Aldara®), for which there are considerable local side-effects (itching, redness, irritation);
  derivatives of methylaminolevulinic acid, which allow a photodynamic therapy. These derivatives are suitable for keratosis with a slight thickness or nonhyperkeratosic, non-pigmented, of the face or scalp and consequently have a relatively limited range of application;
  anti-inflammatory agents based on diclofenac (Solaraze®), suitable for less serious situations;
  topical 5-fluorouracyl (Efudex® ointment); as in the case of retinoids and immunomodulators, the side-effects are rather heavy, both in terms of local action (redness, itching, formation of blisters, desquamation, contact dermatitis) and systemic action. 5-Fluorouracyl is in fact consistently absorbed and, among other things, can cause alterations of the sperm and leucocytosis. Its use is therefore limited to high-risk situations.

The necessity is therefore strongly felt for a topical pharmacologic treatment which is active against the various forms of actinic keratosis, and has a low toxicity, which is easy to administer and with limited local and/or systemic side-effects.

An objective of the present invention is therefore to find pharmaceutical compositions which overcome the drawbacks mentioned above, which are present in the pharmaceutical compositions described and used in the state of the art for the topical pharmacological treatment of various forms of actinic keratosis and, more generally, other types of hyperproliferative skin diseases.

The present invention satisfies this necessity thanks to pharmaceutical compositions based on a conjugate between hyaluronic acid (or a derivative thereof) and antitumoral drugs.

The Applicant has in fact surprisingly found that the use of these pharmaceutical compositions is characterized by a high effectiveness, safety and low toxicity in the topical treatment of the pre-cancerous pathology described, i.e. in actinic keratosis, and also in the treatment of other types of hyperproliferative skin diseases, such as psoriasis, or in the treatment of tumoral forms in situ such as squamous cellular carcinoma.

An object of the present invention therefore relates to the use of a conjugate between hyaluronic acid or a derivative thereof and antitumoral drugs for the preparation of a pharmaceutical composition for the topical treatment of hyperproliferative skin diseases, preferably for the topical treatment of actinic keratosis, psoriasis or in the treatment of tumoral forms in situ such as squamous cellular carcinoma, even more preferably for the topical treatment of actinic keratosis.

The pharmaceutical composition is preferably based on a conjugate between hyaluronic acid or a derivative thereof and an antitumoral drug selected from paclitaxel or 5-fluorouracyl, more preferably the antitumoral drug is paclitaxel.

Even more preferably, the HA-paclitaxel conjugate corresponds to HA/paclitaxel conjugated ester having a substitution degree equal to 20% w/w.

The HA-5-fluorouracyl conjugate preferably corresponds to the conjugated ester having a substitution degree equal to 15% w/w.

Conjugates between hyaluronic acid or a derivative thereof and paclitaxel are already known in the state of the art (patent application EP 1560854) and have proved to be effective in the systemic treatment of numerous tumoral forms.

The HA-5-fluorouracyl conjugation is described in patent application WO2007/14784, to which reference is made herein for each characteristic relating to the chemical synthesis of the compound and its characteristics. As specified above, the use of 5-fluorouracyl in actinic keratosis described in the state of the art is greatly limited by significant side-effects. The bond with HA makes the active principle much less toxic after topical administration, as it allows its permanence only at the level of the lesion to be treated, avoiding its systemic accumulation.

A fundamental advantage of the pharmaceutical compositions used according to the present invention is that they remain in the application site and are progressively released, without systemic absorption.

A further advantage of the pharmaceutical compositions used according to the present invention is that the heavy side-effects of the active principles adopted are drastically reduced. They also allow the irritating and desquamating effects which normally arise in the treatment of the pathologies described, to be minimized.

DETAILED DESCRIPTION OF THE INVENTION

The present invention describes and claims the use of conjugates between hyaluronic acid or a derivative thereof and an antitumoral drug, active on cellular proliferation, said drug preferably being paclitaxel or 5-fluorouracyl, even more preferably paclitaxel, in the preparation of pharmaceutical compositions for the topical therapy of hyperproliferative skin diseases, and in particular actinic keratosis.

As already mentioned, HA-paclitaxel conjugates are known in the state of the art; their preparation and systemic use in various kinds of neoplasias are described in EP 1560854, whose contents form an integrant part of the present invention relating to every aspect of the synthesis of the conjugates.

HA-paclitaxel conjugates are molecules obtained from the conjugation, i.e. creation of a chemical bond of the ester or amide type, between hyaluronic acid or a derivative thereof and paclitaxel.

The bond can be direct, when HA and the drug are directly joined to each other, or indirect, when the bond occurs through a "spacer" which acts as a molecular bridge. Aliphatic chains of various lengths are normally used as spacers, which, among others, can be bromo-butyric or bromo-propionic chains. The conjugation modifies the pharmacokinetic properties of paclitaxel, making it more stable and hydrosoluble; the possibility of operating with aqueous vehicles makes the use, in the various formulations, of oily solubilizers such as Cremofor, ineffective, and this drastically reduces the formation of undesired effects associated with the toxicity of these substances.

As far as HA-5-Fluorouracyl is concerned, its preparation and characteristics are described in WO2007/14784; also in this case, the pharmacological active principle and HA are bound by means of a spacer which can be bromo-butyric or bromo-propionic, by the formation of ester or amide bonds. The HA-5-Fluorouracyl conjugate thus obtained is a molecule which has better hydrosolubility characteristics and resistance to degradation with respect to the active principle as such, as the active principle is "protected" by the hyaluronic acid to which it is bound.

The possibility of obtaining pharmaceutical compositions having rheological properties widely differing from each other is of fundamental importance for the applications described herein: this depends on the intrinsic characteristics of HA, whose molecule, before being conjugated with the pharmaceutical active principle, can be greatly modified through various chemical reactions. Chemical modifications known in the state of the art are those described, among others, in EP 1,560,854, and more specifically are salification with organic and/or inorganic bases (EP 0138572 B1), esterification with alcohols of the aliphatic, araliphatic, cyclo-aliphatic, aromatic, cyclic and heterocyclic series (Hyaff®, EP 216453 B1), amidation with amines of the aliphatic, araliphatic, cyclo-aliphatic, aromatic, cyclic and heterocyclic series (HYADD®, EP 1095064 B1), O-sulfation (EP 0702699 B1), internal esterification (ACP®, EP 0341745 B1), deacetylation, percarboxylation (Hyoxx®, EP 1313772 B1).

The derivatives obtained through these reactions preserve the biological characteristics of the starting polysaccharide, but have better mechanical properties; they can also be easily formulated in the form of hydrogels, creams, ointments, films, plasters, nonwovens, etc., and therefore allow a wide range of topical pharmaceutical forms to be produced, completely adaptable to each individual therapeutic demand.

As far as the characteristics of the hyaluronic acid used for the purposes of the present invention are concerned, reference should be made to what is described in EP 1560854 and in WO2007/14784.

Briefly summarizing, the hyaluronic acid which can be used in the present invention can derive from any source, for example by extraction from rooster's combs (EP 0138572) or fermentatively (EP 0716688), and have a molecular weight ranging from 400 to 3,000,000 Da, in particular from 50,000 to 1,000,000 Da.

The derivatives of hyaluronic acid which can be used in the preparation of the conjugates object of the present invention, are the following:

1) salts with organic and/or inorganic bases also biologically active (EP 138572 B1);

2) HYAFF®: esters of hyaluronic acid with alcohols of the aliphatic, araliphatic, cyclo-aliphatic, aromatic, cyclic and heterocyclic series with an esterification percentage which can vary according to the type of alcohol and length of the alcohol used (EP 216453 B1);

3) HYADD®: amides of hyaluronic acid with amines of the aliphatic, araliphatic, cyclo-aliphatic, aromatic, cyclic and heterocyclic series (EP 1095064 B1);

4) O-sulfated derivatives (EP 0702699 B1) of hyaluronic acid (AP 0971961 A1);

5) ACP®: internal esters of hyaluronic acid with an esterification percentage not higher than 20% (EP 0341745 B1);

6) deacetylates of HA: the N-acetyl-glucosamine fraction is deacetylated with a deacetylation percentage preferably ranging from 0.1 to 30% (EP 1313772 B1);

7) percarboxylates of HA obtained from the oxidation of the primary hydroxyl of the N-acetyl-glucosamine fraction with a percarboxylation degree ranging from 0.1 to 100% (HYOXX®, EP 1339753 A1).

In particular, the HA-paclitaxel conjugate is preferably obtained by means of a covalent bond between paclitaxel and an ester of HA, it can be obtained starting from chemically non-modified HA molecules and effecting possible modifications of HA only after the synthesis of the conjugate with the active principle.

The covalent bond can be direct or by means of a spacer also in the case of the HA-paclitaxel conjugate. In particular, the process for preparing the HA-paclitaxel conjugate wherein the active principle paclitaxel is covalently bound to HA or a derivative thereof, can be a process by means of indirect synthesis with the introduction of a spacer between the paclitaxel and HA or a derivative thereof; or a direct synthesis process between paclitaxel and HA or a derivative thereof. The possible reaction schemes either direct or indirect for the synthesis of the HA-paclitaxel conjugate as already indicated are described in detail in the document WO2004/035629 and are considered an integrant part of the present patent application.

The synthesis of the HA-paclitaxel conjugate is described, for purely illustrative purposes, by means of the method indicated in scheme 1 below:

Scheme 1

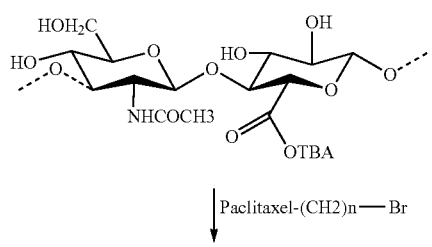

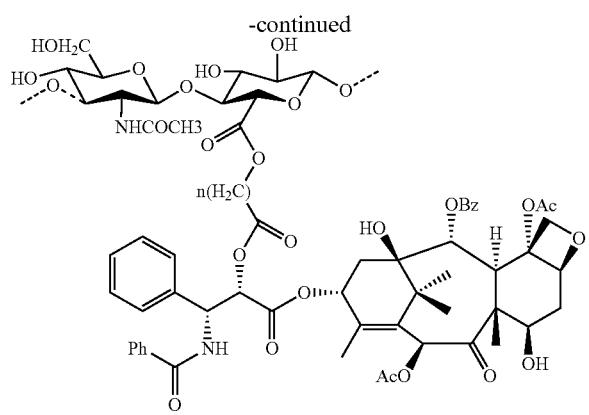

As previously indicated, the use of the HA-paclitaxel conjugate corresponding to the ester of the HA/paclitaxel conjugate having a substitution degree equal to 20% w/w, is preferred.

Scheme 2 is also provided hereunder relating to the synthesis of the HA-paclitaxel conjugated (ester at 20% of HA with paclitaxel through the Bromo-butyric spacer):

Scheme 2

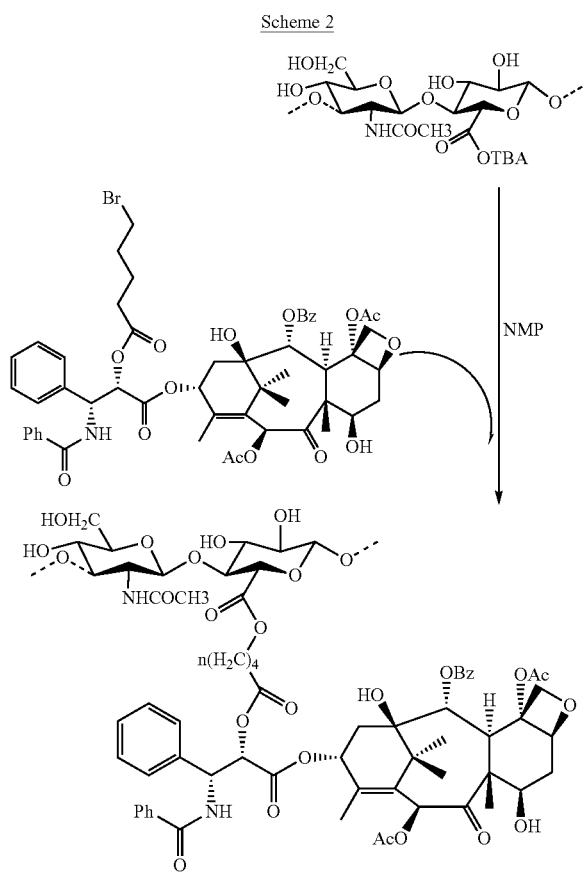

The HA-5-fluorouracyl conjugate, on the other hand, is obtained by the formation of an indirect covalent bond between HA or a derivative thereof and the active principle by means of a spacer which forms an ester or amide bond with the carboxylic group of HA or a derivative thereof. The preferred spacers are bromo-butyric or bromo-propionic acid.

In particular, the HA-5-fluorouracyl conjugate is obtained by the indirect bond between HA or a derivative thereof and 5-fluorouracyl by means of a spacer through the formation of ester bonds according to the following procedure:

a suitable functional group of the spacer, also containing a second group capable of reacting with the carboxylic function of HA, reacts with a functional group belonging to the active principle. The reaction may possibly require an activation. In a subsequent phase, by direct contact between a tetra-alkylammonium salt of HA in an anhydrous environment, the compound consisting of the modified active principle reacts giving rise to a nucleophilic substitution of the outgoing group at the HA carboxyl, forming an ester bond between HA and the spacer.

Alternatively, it is possible to first react a carboxyl group of HA with the spacer (nucleophilic substitution) and subsequently bind the spacer to a function of the antitumoral active principle.

Other methods are well-known to experts in the field and described in detail in WO2007/014784 for the formation of the conjugate through the formation of an amide bond.

As previously observed, the derivatives obtained through these reactions maintain the biological characteristics of the starting polysaccharide, but they have better mechanical properties; they can also be easily formulated in the form of hydrogels, creams, ointments, films, plasters, nonwovens, etc., and therefore allow the production of a wide range of topical pharmaceutical forms, which can be completely adapted to each single therapeutic requirement.

In particular, therefore, the topical pharmaceutical composition used according to the present invention is formulated in the form of creams, hydrogels, ointments or in the form of medicated plasters or films containing the conjugate. These formulations envisage a quantity of conjugate between HA or a derivative thereof and the antitumoral drug or active principle which varies from 0.05 to 10% by weight, preferably from 0.2 to 5% by weight with respect to the total weight of the composition.

The complement to 100 of the composition according to the present invention consists of pharmacologically acceptable additives, typical of topical formulations and water.

Examples of topical formulations of the pharmaceutical composition according to the present invention are indicated in the following tables for purely illustrative purposes (the percentages indicated are weight %).

TABLE 1

| Cream formulation | |
|---|---|
| Component | % |
| 1.a | |
| HA-paclitaxel conjugate | 1% |
| Emulsifying wax | 0.5% |
| Decyl oleate | 1.25% |
| Sorbitol | 0.4% |
| Methyl p-hydroxybenzoate | 0.05% |
| Glycerol | 0.4% |
| PEG 400 monostearate | 2.5% |
| Sodium Dehydroacetate | 0.05% |
| Propyl p-hydroxybenzoate | 0.005% |
| Aromas | 0.01% |
| Water | Complement to 100 |
| 1.b | |
| HA-paclitaxel conjugate | 2.5% |
| Emulsifying wax | 0.5% |
| Decyl oleate | 1.25% |

TABLE 1-continued

Cream formulation

| Component | % |
|---|---|
| Sorbitol | 0.4% |
| Methyl p-hydroxybenzoate | 0.05% |
| Glycerol | 0.4% |
| PEG 400 monostearate | 2.5% |
| Sodium Dehydroacetate | 0.05% |
| Propyl p-hydroxybenzoate | 0.005% |
| Aromas | 0.01% |
| Water | Complement to 100 |
| *1.c* | |
| HA-paclitaxel conjugate | 5% |
| Emulsifying wax | 0.5% |
| Decyl oleate | 1.25% |
| Sorbitol | 0.4% |
| Methyl p-hydroxybenzoate | 0.05% |
| Glycerol | 0.4% |
| PEG 400 monostearate | 2.5% |
| Sodium Dehydroacetate | 0.05% |
| Propyl p-hydroxybenzoate | 0.005% |
| Aromas | 0.01% |
| Water | Complement to 100 |

TABLE 2

Hydrogel formulation

| Component | % |
|---|---|
| *2.a* | |
| HA-paclitaxel conjugate | 1% |
| Carbopol | 1.5% |
| Vegetable glycerol | 6.7% |
| Propylene glycol | 0.2% |
| Triethanolamine | 1.3% |
| Polyethylene glycol | 6.7% |
| Propyl p-hydroxybenzoate | 0.2% |
| Methyl p-hydroxybenzoate | 0.2% |
| Water | Complement to 100 |
| *2.b* | |
| HA-paclitaxel conjugate | 2.5% |
| Carbopol | 1.5% |
| Vegetable glycerol | 6.7% |
| Propylene glycol | 0.2% |
| Triethanolamine | 1.3% |
| Polyethylene glycol | 6.7% |
| Propyl p-hydroxybenzoate | 0.2% |
| Methyl p-hydroxybenzoate | 0.2% |
| Water | Complement to 100 |
| *2.c* | |
| HA-paclitaxel conjugate | 5% |
| Carbopol | 1.5% |
| Vegetable glycerol | 6.7% |
| Propylene glycol | 0.2% |
| Triethanolamine | 1.3% |
| Polyethylene glycol | 6.7% |
| Propyl p-hydroxybenzoate | 0.2% |
| Methyl p-hydroxybenzoate | 0.2% |
| Water | Complement to 100 |

TABLE 3

Cream formulation

| Component | % |
|---|---|
| HA-5-fluorouracyl conjugate | 2.5% |
| Emulsifying wax | 0.5% |
| Decyl oleate | 1.25% |

TABLE 3-continued

Cream formulation

| Component | % |
|---|---|
| Sorbitol | 0.4% |
| Methyl p-hydroxybenzoate | 0.05% |
| Glycerol | 0.4% |
| PEG 400 monostearate | 2.5% |
| Sodium Dehydroacetate | 0.05% |
| Propyl p-hydroxybenzoate | 0.005% |
| Aromas | 0.01% |
| Water | Complement to 100 |

TABLE 4

Hydrogel formulation

| Component | % |
|---|---|
| HA-5-fluorouracyl conjugate | 2.5% |
| Carbopol | 1.5% |
| Vegetable glycerol | 6.7% |
| Propylene glycol | 0.2% |
| Triethanolamine | 1.3% |
| Polyethylene glycol | 6.7% |
| Propyl p-hydroxybenzoate | 0.2% |
| Methyl p-hydroxybenzoate | 0.2% |
| Water | Complement to 100 |

TABLE 5

Ointment formulation

| Component | % |
|---|---|
| *5.a* | |
| HA-paclitaxel conjugate | 1% |
| Light liquid paraffin | 20% |
| Stringy vaseline | Complement to 100 |
| *5.b* | |
| HA-paclitaxel conjugate | 2.5% |
| Light liquid paraffin | 20% |
| Stringy vaseline | Complement to 100 |
| *5.c* | |
| HA-paclitaxel conjugate | 5% |
| Light liquid paraffin | 20% |
| Stringy vaseline | Complement to 100 |

The following in vitro and in vivo tests carried out on mice in which actinic keratosis was induced demonstrate that the antitumoral drug or active principle conjugated with HA or a derivative thereof is effective, it remains in the application site and is progressively released without there being systemic absorption. In this way the heavy side-effects of the active principles used, which exert an antiproliferative action, are drastically reduced; thanks to the regenerating, cicatrizing and moistening properties of HA, moreover, the irritating and desquamating effects which normally arise in the treatment of the pathologies described, are minimized.

The present invention is now described for illustrative but non-limiting purposes according to its preferred embodiments with particular reference to the figures of the enclosed drawings, in which.

EXAMPLE 1

Figure 1:
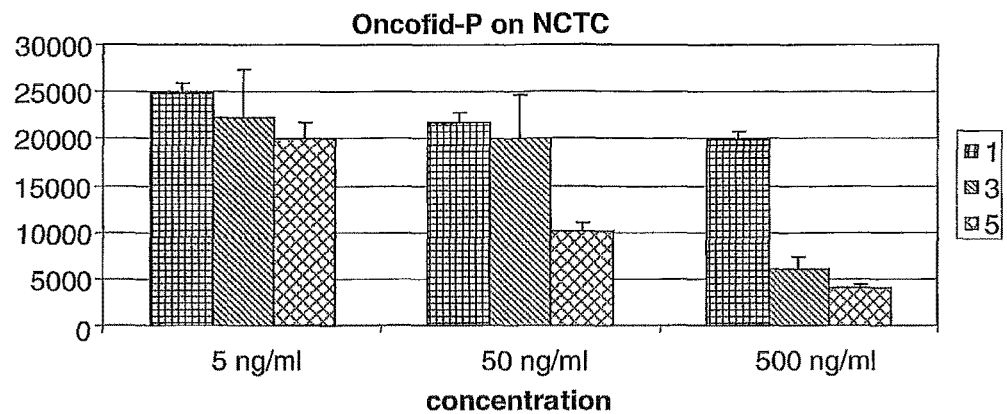
FIG. 1 shows the graph of the results of the MTT test carried out on immortalized line keratinocytes (NCTC-2544) which illustrates the proliferative activity of the keratinocytes in response to different concentrations of conjugate (5 ng/ml, 50 ng/ml e 500 ng/ml)

Evaluation of the Antiproliferative Activity of HA/Paclitaxel Conjugated Ester Having a Substitution Degree Equal to 20% w/w on the Immortalized Cellular Line of NCTC-2544 Keratinocytes and Primary Human Keratinocytes In order to verify the antiproliferative activity of the HA/paclitaxel conjugate, various in vitro experiments were effected suitable for evaluating the proliferative activity of the immortalized cellular line of NCTC-2544 keratinocytes and primary human keratinocytes.

Experimental Design

In particular, the tests were directed towards identifying concentrations of the HA/paclitaxel conjugate at which healthy primary keratinocytes and keratinocytes of an immortalized cellular line NCTC-2544:

die;

slow down their proliferative activity;

survive

The optimum cell plant conditions were first determined to guarantee that the cell confluence had been reached at the $5^{th}$ culture day.

The cells were then cultivated in a single-layer at different concentrations of HA/paclitaxel conjugate previously dissolved in the culture medium.

The cell proliferation following treatment was evaluated at pre-established times, 1, 3, and 5 days, by an incorporation test of bromodeoxyuridine and an MTT Test.

Materials and Methods

Materials:

HA/paclitaxel conjugate: HA/paclitaxel conjugated ester having a substitution degree equal to 20% w/w Cellular Lines:

immortalized cell line of NCTC-2544 keratinocytes primary human keratinocytes

Methods:

Isolation of healthy keratinocytes from human skin biopsies: after various washings in PBS containing antibiotics, the skin biopsy was cleaned of the adipose subcutaneous tissue and cut into small strips. These strips were digested with dispase for 30 minutes. At the end of the treatment the skin was separated from the underlying dermis and digested with tripsin for 10 minutes.

NCTC-2544 culture: the cells were cultivated in vitro in DMEM medium (Dulbecco Modified Eagle Medium) supplemented with fetal bovine serum 20%; P/S (penicillin/streptomycin) 1%; Glutamine 1%.

Bromodeoxyuridine Incorporation Test (BRDU):

After incorporation of bromodeoxyuridine (BrdU, analogous to thymine), the cells were subjected to marking with anti-BrdU antibody and subsequently analyzed with a plate. The marking with BrdU is used as a cell proliferation index. MTT test: the cells were incubated with a solution of MTT (3-(4,5-dimethylthiazol-2-yl)-2,5-dihpenyltetrazole) 0.5 mg/ml for 3 hours. At the end of the incubation, the MTT dye was extracted from the cells using an extracting solution (90% isopropanol, 10% DMSO). The dye is read at 540 nm/660 nm.

Cell seeding tests: the line cells (NCTC) and healthy keratinocytes were plated on plates having 24 wells at three different concentrations, 3,000-6,000-12,000 cells per well. The cell confluence was then evaluated by microscope analysis.

Preparation of the solution of HA/paclitaxel conjugate: the HA/paclitaxel conjugate was dissolved in a glucosate solution at 5% by weight. The solution of the HA/paclitaxel conjugate was subsequently filtered with filters made of Cellulose-Acetate Cod. Albet having a diameter of 25 mm and Cut-off of 0.20 microns.

Preparation of the glucosate solution at 5% by weight: 5 g of anhydrous glucose were weighed and dissolved in 100 ml of distilled water. The solution was sterilized with a 0.22 micron filter.

Treatment with the HA/paclitaxel conjugate: 6 series of experiments were carried out at different concentrations of HA/paclitaxel conjugate.

a) 10 mg/ml; 6 mg/ml, 2 mg/ml,
b) 2 mg/ml; 1 mg/ml, 0.5 mg/ml,
c) 0.125 mg/ml; 0.050 mg/ml, 0.025 mg/ml,
d) 0.025 mg/ml; 0.0125 mg/ml and 0.005 mg/ml,
e) 0.001 mg/ml and 0.0005 mg/ml,
f) 500 ng/ml, 50 ng/ml and 5 ng/ml 3.

Results

As indicated in the section of materials and methods, the cells were seeded in plates having 24 wells at three different concentrations, 3,000-6,000-12,000 cells per well. The cell confluence was then evaluated by microscope analysis. Following this evaluation, it was established that the initial seeding concentration equal to 6,000 cells per well, allows the confluence to be reached 5 days after seeding.

Activity of the HA/Paclitaxel Conjugate $1^{st}$ series of selected concentrations:

10 mg/ml, 6 mg/ml and 2 mg/ml;

$2^{nd}$ series of selected concentrations:

2 mg/ml, 1 mg/ml and 0.5 mg/ml.

At the above concentrations, 24 hours after administration of the drug, upon observing the wells under the microscope, the cells proved to be dead at all the treatment concentrations.

The cell proliferation test was in any case carried out using, as positive control, cells treated with a solution of SDS (sodium dodecyl sulfate) 0.4%. The results of this analysis confirmed the cell death for all the samples treated.

$3^{rd}$ series of selected concentrations:

0.125 ml/ml, 0.050 mg/ml and 0.025 mg/ml;

$4^{th}$ series of selected concentrations:

0.025 mg/ml, 0.0125 mg/ml and 0.005 mg/ml;

$5^{th}$ series of selected concentrations:

0.001 mg/ml and 0.0005 mg/ml.

In all these tests, the HA-antitumoral conjugate was administered at 10.00 o'clock of the morning following the planting of the cells; at 15.00 o'clock, therefore 5 hours later, at the moment of the administration of BrdU for incorporation on the part of the cells, these already appeared to have become rounded; even if still adhering to the substrate, in spite of this, the decided tests were carried out.

The test which evaluates the cell proliferation through the incorporation of BrdU gave values comparable to the positive control wells (with the dead cells) at all the concentrations tested, consequently no cell proliferation activity was found in the presence of the HA/paclitaxel conjugate.

The same result was obtained with the MTT test.

$6^{th}$ series of selected concentrations 500 ng/ml, 50 ng/ml and 5 ng/ml.

Figure 2:
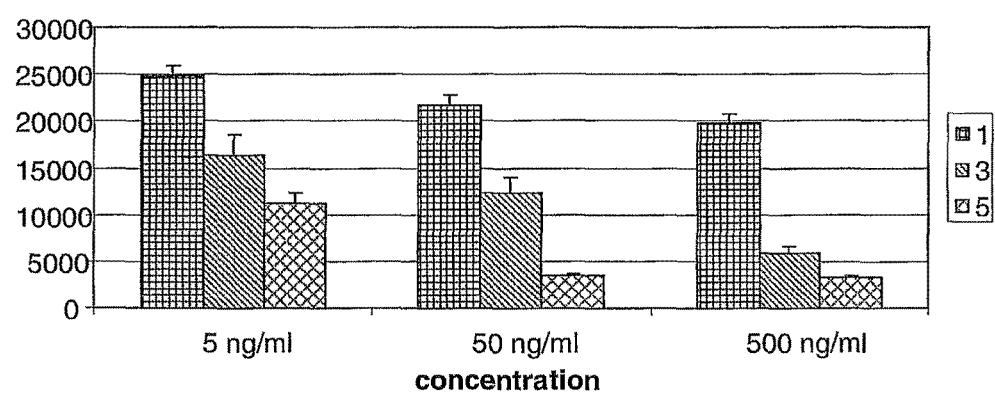
FIG. 2 shows the graph of the results of the MTT test carried out on healthy primary keratinocytes which illustrates the proliferative activity of the keratinocytes in response to different concentrations of conjugate (5 ng/ml, 50 ng/ml e 500 ng/ml)

As can be observed from the graphs indicated in FIGS. 1 and 2, these concentrations influence the proliferative activity of both the keratinocytes of the line and healthy primary keratinocytes.

In particular, the concentration of 500 ng/ml causes a massive reduction in cell proliferation with time. The values relating to proliferation are in fact drastically reduced from day 1 to day 5.

The concentration of 50 ng/ml causes a slowing-down of the cell proliferation, in particular starting from day 5. This event is evident in the line keratinocytes whereas in the primary keratinocytes, a drop in the cell proliferation is already observed starting from the $3^{rd}$ day of treatment.

The concentration of 5 ng/ml does not seem to cause any significant effects on the proliferative activity in the keratinocytes of the line (NCTC-2544): the cells survive and maintain their proliferative activity until the $5^{th}$ day, whereas in the case of healthy primary keratinocytes, a drop in the cell proliferation is observed starting from day 3.

Conclusions

In the light of the results previously indicated, it can be concluded that concentrations higher than 500 ng/ml are highly toxic for the cells as they cause their death within 24 hours of administration; concentrations lower than 5 ng/ml do not cause any antiproliferative effects on the line cells, whereas concentrations much lower than 5 ng/nl do not cause any antiproliferative effects on healthy keratinocytes.

Analogous tests to those effected in example 1 are also being carried out to evaluate the antiproliferative activity of the ester of the HA/5-fluorouracyl conjugate having a substitution degree equal to 15% w/w on the immortalized cell line of NCTC-2544 keratinocytes and primary human keratinocytes. These preliminary tests gave results which confirm a trend comparable to that of the HA/paclitaxel conjugate.

EXAMPLE 2

Evaluation of the Activity of the HA/Paclitaxel Conjugate in an In Vivo Model of Actinic Keratosis In order to evaluate the activity of the HA/Paclitaxel bioconjugate in the treatment of hyperproliferative dermatological pathologies, and more specifically in the treatment of actinic keratosis, a model of Actinic Keratosis (AK) was prepared, which in relatively short periods of time inevitably degenerates into Squamous Cell Carcinoma (SCC), in SHK-R1' hairless mice, considered in literature as being suitable for this type of experimentation (De Gruijl F R and Forbes P D. BioEssays 1995; 17:651-60; Kligman L H and Kligman A M. JNCI 1981; 67:1289-97). As already specified, in fact, actinic keratosis is considered a precancerous form, degenerating into squamous cell carcinoma, also known as spinocellular carcinoma.

Materials and Methods

Experimental Protocol

20 SHK-R1' mice aged 6-7 weeks were used, divided into four groups of five:
group A: control.
group B: animals treated with the HA/paclitaxel conjugate 1% cream, prepared as formulation 1.a
group C: animals treated with Efudex® Ointment (5-FluoroUracyl)
group D: animals treated with Connettivina® Cream (HA 0.2%).

The latter group allows an evaluation as to whether the positive effect of the preparation being tested is exclusively due to the presence of hyaluronic acid, whose healing properties are well-known.

The topical use of Paclitaxel alone was not possible due to the excessive irritating action of the active principle, completely unsuitable for this form of administration as it has to be solubilized in Cremofor (Beri R, Rosen F R, Pacini M j, Desai S R. Severe dermatologic reactions at multiple sites after paclitaxel administration. *Ann. Pharmacother* 2004; 38, 238-41; Baycal C, Erkel E, Tutar E, Yuce K, Ayhan A. Cutaneous fixed drug eruption to paclitaxel; a case report. *Eur. J. Gynaecol. Oncol.* 2000; 21, 190-1)

All the animals were irradiated on their dorsal area 3 times a week for 30 minutes with the UVB irradiating source Jelolamp FS40_(Jelosil Skin UVS 311 nm; Jelosil srl, Vimodrone—Italy) with broad band situated 30 cm from the mice. By calculating the distance of each mouse from the source, which is variable as the animals lie in different positions under the irradiation source, the irradiation was evaluated as being equal to 540÷1080 mJ/cm$^2$. After a period of about 2 weeks, the mice had evident signs of skin erythema on their backs.

Figure 3:
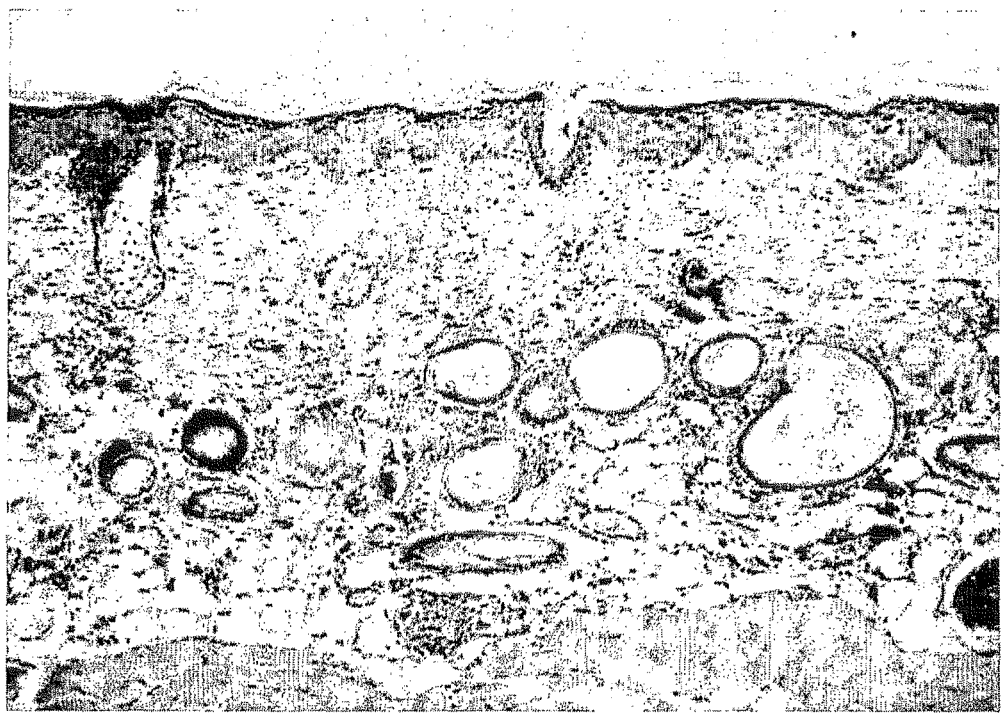
FIG. 3 shows the histological examination of the lesions after 8-9 weeks of irradiation.
Figure 4:
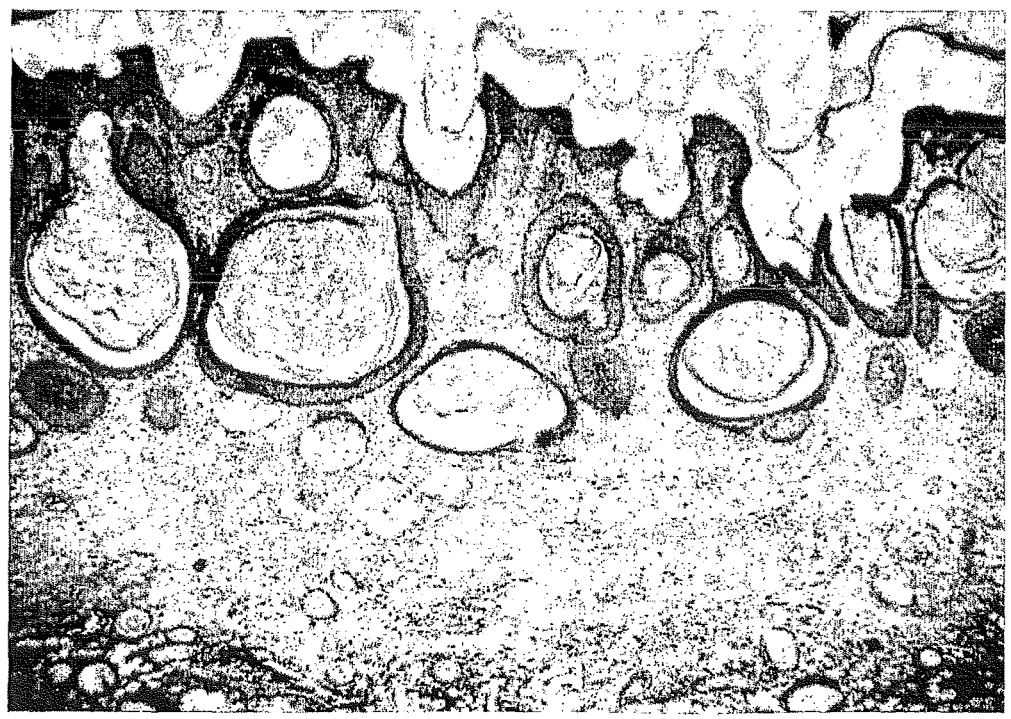
FIG. 4 shows the histological examination of the lesions after 8-9 weeks of irradiation with upper magnification.

In all of the animals, after 8-9 weeks, a lesion had developed on their backs and heads, which clinically appeared as a hyperkeratotic plaque (with dimensions of 2.5 cm×1 cm), having an irregular, almost verrucous, surface. A histological examination of these lesions revealed (FIGS. 3 and 4):

Hyperplastic epidermis, with hypergranulosis, acanthosis and hyperkeratosis.

Absence of cytological atypicalness and signs of dermal invasion.

Presence of large-sized cysts, containing abundant keratinic matter, in some cases with extroversion on the outside of the epidermis.

After 15÷16 weeks, papular, cupuliform lesions, having a translucent appearance and dimensions of 1-2 mm, appeared on the backs and heads of the mice.

After 15÷18 weeks of UVB irradiation, all the animals had developed hyperkeratotic plaques on the surface of the skin, which could be attributed to the manifestation of the pathology in question: at this point, groups B, C and D were treated with the formulations indicated above.

The preparations were applied on the lesioned skin, for 14 consecutive days.

During the period of treatment, the death of all of the animals of group C, treated with Efudex® Ointment, was verified, in the interval between the $10^{th}$ and $13^{th}$ day, further demonstrating the high toxicity of 5-FU which is massively absorbed systemically; none of the animals of the other groups, on the contrary, showed any signs of intolerance to the formulations and there were no spontaneous deaths.

The treatment with the HA/paclitaxel conjugate 1% did not cause any visible skin reaction in the animals, unlike what would have occurred with Paclitaxel alone.

Figure 5:
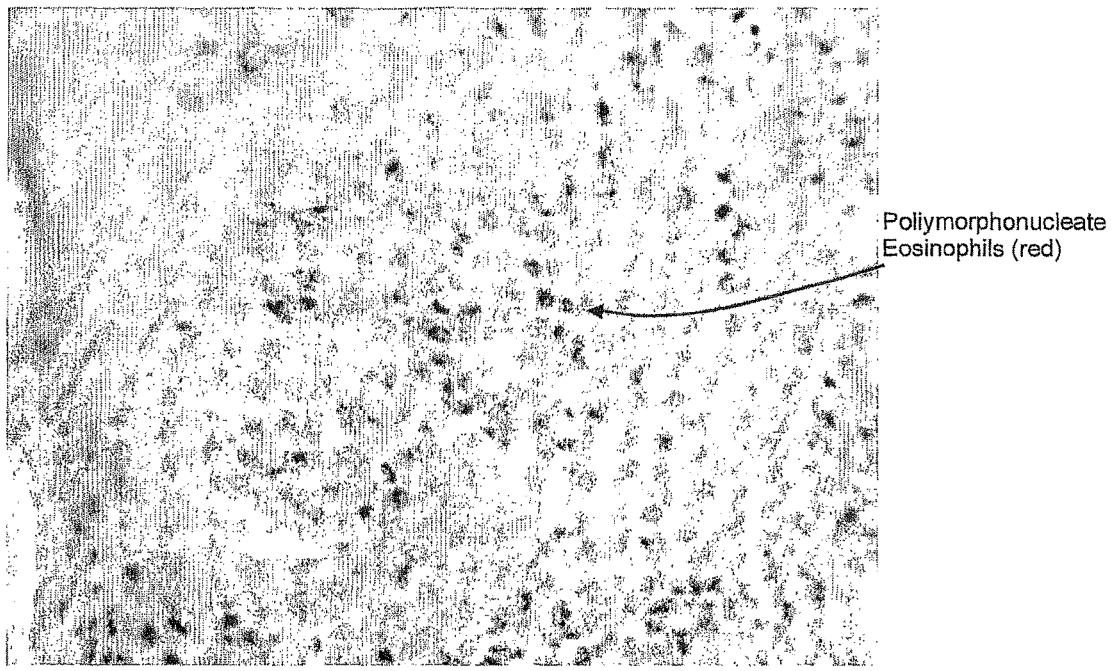
FIG. 5 shows the histological examination of the lesioned skin after application of the preparation based on the conjugate according to the invention, from which the presence of eosinophilic polymorphonucleates (visible in red and indicated by the arrow), index of an inflammatory process underway, prodromic of the skin reparatory phase, can be observed.

From a histological point of view, the presence of numerous eosinophilic polymorphonucleates was observed in the above-mentioned preparation, indicating an inflammatory process underway, prodromic of the skin reparatory phase (FIG. 5). A progression of the skin lesions was observed, on the other hand, in both the group of animals treated with Connettivina® Cream and in the non-treated group.

Results

From a histological analysis effected on the biopsies taken from the above treatment groups, the following conclusions can be reached:

- no superiority of Connettivina® Cream in slowing down the degeneration of AK in SCC with respect to the non-treated reference;
- evident superiority of the HA/paclitaxel conjugate 1% in significantly slowing down said degeneration with respect to Connettivina® Cream and the non-treated reference group. The presence of eosinophilic polymorphonucleates preludes and is an integrant part of the formation phase of granulation tissue, re-epithelization and re-modelling, essential for healing the hyperkeratotic plaque of AK.

It can therefore be asserted that:

- treatment with the HA/Paclitaxel conjugate 1% in a cream vehicle significantly slows down the degeneration of hyperkeratotic plaques to SCC in the selected animal model;
- furthermore, treatment with the HA/Paclitaxel conjugate 1% in a cream vehicle induces the presence of eosinophilic polymorphonucleates, necessary for the granulation, re-epithelization and re-modelling of skin tissue suffering from plaques;
- the formulation presented does not create any problem of skin irritation following topical application;
- as no animal died or showed signs of suffering, it can be deduced that paclitaxel is substantially released in loco and is not subject to significant systemic absorption.

Conclusions

In conclusion, the HA/Paclitaxel conjugate 1% in a cream vehicle described herein proved to be effective in the treatment of AK, as it repaired hyperkeratotic lesions and contemporaneously significantly slowed down the degeneration of the pathology towards its neoplastic form.

The invention claimed is:

1. A method of treating KA (actinic keratosis) with a conjugate of hyaluronic acid (HA) or a derivative thereof and paclitaxel, without systemic absorption of said paclitaxel, which comprises the topical administration of said conjugate to a patient in need thereof, wherein said conjugate comprises a conjugated ester formed at carboxyl groups of HA with a bromobutyric spacer and a substitution degree of 20% w/w, and wherein said conjugate remains only at the location of the lesion that is treated with said topical administration, whereby systemic accumulation of said conjugate is avoided.

2. The method according to claim 1, wherein said conjugate is administered in a pharmaceutical composition in the form of a cream, hydrogel, ointment or in the form of medicated plasters or films.

3. The method according to claim 2, wherein the conjugate between HA or a derivative thereof, and paclitaxel ranges from 0.05 to 10% by weight, with respect to the total weight of the composition.

4. The method according to claim 2, wherein the conjugate between HA or a derivative thereof, and paclitaxel ranges from 0.2 to 5% by weight, with respect to the total weight of the composition.

* * * * *